United States Patent [19]

Herlihy et al.

[11] Patent Number: 4,629,792
[45] Date of Patent: Dec. 16, 1986

[54] CHROMATOGRAPHIC SEPARATION OF TROPICAMIDE O-β-D-GLUCURONIDE DIASTEREOMERS

[75] Inventors: Walter C. Herlihy, Cambridge; Thomas H. Fraser, Newtonville, both of Mass.

[73] Assignee: Repligen Corporation, Cambridge, Mass.

[21] Appl. No.: 773,714

[22] Filed: Sep. 9, 1985

Related U.S. Application Data

[62] Division of Ser. No. 575,521, Jan. 31, 1984, Pat. No. 4,588,686, which is a division of Ser. No. 381,528, May 24, 1982, Pat. No. 4,443,608.

[51] Int. Cl.$^4$ .................. C07H 15/26; B01D 15/08
[52] U.S. Cl. .................................. 546/268; 424/60; 435/77; 435/280; 435/803; 536/17.3
[58] Field of Search .............. 546/268; 536/17.3; 424/60; 435/77, 122, 129, 137, 280, 97, 803; 210/635, 656, 657, 658, 659

[56] References Cited

U.S. PATENT DOCUMENTS

| | | | |
|---|---|---|---|
| 3,240,777 | 3/1966 | Sarett | 260/239.55 |
| 4,153,697 | 5/1979 | Hornke | 424/258 |
| 4,292,250 | 9/1981 | Deluca | 260/397.2 |
| 4,476,300 | 10/1984 | Herlihy | 546/268 |
| 4,478,936 | 10/1984 | Herlihy | 435/137 |

OTHER PUBLICATIONS

Ando, et al., Synthesis of Mycophenolic Acid β-D-Glucuronide and its Antitumor Activity, J. Antibiotics, 23, 408-413 (1970).
Johnson, et al., Glucuronidation of Lipophilic Substrates, Prep. Biochem. 9, 391-406 (1979).

Primary Examiner—Ernest G. Therkorn
Attorney, Agent, or Firm—Roman Saliwanchik

[57] ABSTRACT

An in vitro enzymatic process which efficiently converts (+,−)-tropicamide to essentially pure (+), (−)-tropicamide O-β-D-glucuronide. This product is then separated, advantageously, into the novel compounds (+)-tropicamide O-β-D-glucuronide and (−)-tropicamide O-β-D-glucuronide. The products disclosed herein absorb ultraviolet light, and, thus, can be incorporated into suitable plastic films which are then useful for screening out harmful ultraviolet radiation for the protection of packaged goods. Also, the products can be used to protect the skin against burning by sunlight.

2 Claims, No Drawings

CHROMATOGRAPHIC SEPARATION OF TROPICAMIDE O-β-D-GLUCURONIDE DIASTEREOMERS

The present application is a divisional application of Ser. No. 575,521, Jan. 31, 1984, now U.S. Pat. No. 4,588,686, which is a divisional of Ser. No. 381,528, May 24, 1982, U.S. Pat. No. 4,443,608.

BACKGROUND OF THE INVENTION

The preparation of β-glucuronides has been carried out by a number of different techniques. Chemical synthesis typically involves condensation of a suitably protected aglycon with an alkyl (2,3,4-tri-O-acetyl-β-D-glucopyranosyl halide) glucuronate followed by deprotection of the glucuronide and aglycon (Ando, K., Suzuki, S., and Arita, M. [1970] J. Antibiotics 23, 408: Sarett, L. H., Strachan, R. G., and Hirschmass, R. F. [1966] U.S. Pat. No. 3,240,777). A second approach involves feeding large amounts of the aglycon to animals, collecting their urine using and isolating the glucuronide (Hornke, I., Fehlhaber, H. W., Uihlein, M. [1979] U.S. Pat. No. 4,153,697). Alternatively, the animal can be sacrificed and the bile isolated from its gall bladder from which the glucuronide is purified (DeLuca, H. F., Schnoes, H. K., and LeVan, L. W. [1981] U.S. Pat. No. 4,292,250). This in vivo synthesis is catalyzed by the class of enzymes known as uridine diphosphoglucuronyl transferases. In vitro use of this enzyme to produce various β-glucuronides has been reported; for example, a phenolic compound has been glucuronidated (Johnson, D. B., Swanson, M. J., Barker, C. W., Fanska, C. B., and Murrill, E. E. [1979] Prep. Biochem. 9, 391).

BRIEF SUMMARY OF THE INVENTION

Upon incubating liver microsomes in the presence of a suitable buffer to maintain the pH at about 7 to about 8.5, (+,−)-tropicamide, and uridine 5'-diphosphoglucuronic acid (UDPGA), for a sufficient time, there is obtained a preparation of (+),(−)-tropicamide O-β-D-glucuronide. This ammonium salt mixture can be isolated in its essentially pure form by reversed phase chromatography. The diastereomers can be completely resolved to their essentially pure forms by a high pressure liquid chromatographic (HPLC) system disclosed herein.

DETAILED DESCRIPTION OF THE INVENTION

The enzymatic method for the synthesis of β-glucuronides, described herein, has several advantages over prior art chemical synthesis or animal feeding methods. Chemical synthesis requires a minimum of four steps: (1) protection of all the nucleophilic groups in the aglycon except the one involved in the glycosidic linkage, (2) preparation of a suitably protected reactive derivative of D-glucuronic acid, e.g., methyl (2,3,4-tri-O-acetyl-β-D-glucopyranosyl halide) glucuronate, (3) condensation, and (4) deprotection. Complications arise if the aglycon contains functional groups sensitive to the conditions of deprotection. For example, aglycons containing esters or other alkali sensitive linkages can be hydrolyzed during the saponification of the methyl and acetyl protecting groups. In contrast, the enzymatic method described herein involves a single step condensation between a readily available cofactor and the aglycon.

The animal feeding approach to making β-glucuronides also has several disadvantages as compared to the subject enzymatic method. The most significant disadvantage is that stringent purification is required. Other disadvantages are the inconvenience of maintaining animals, and other metabolic pathways including hydroxylation, alkylation, and sulfation can compete with glucuronidation, thus resulting in low yields of the desired product.

The subject enzymatic process for the glucuronidation of (+,−)-tropicamide was unexpectedly successful in view of the fact that attempts to glucuronidate another primary alcohol, i.e., (−)scopolamine, were unsuccessful. Also, there is no known prior art which discloses the preparation of essentially pure (+),(−)tropicamide O-β-D-glucuronide and the two diastereomers (+)-tropicamide O-β-D-glucuronide and (−)-tropicamide O-β-D-glucuronide. The subject process is particularly advantageous because the reaction yields a single pair of stereospecific products, as disclosed above.

The enzymatic reaction, described herein, can be carried out over a pH range of about 7 to about 8.5 with different buffer strengths and with various buffers, for example, sodium N-2-hydroxyethyl piperazine-N'-2-ethanesulfonic acid, tris hydrochloride, and the like. Quantitative glucuronidation can be obtained by increasing the amount of UDP glucuronic acid in the reaction.

The chromatographic methods described herein are based on reversed phase liquid chromatography on C-18 silica supports. This technique is well suited for the purification of enzymatically-produced glucuronides of hydrophobic compounds. Unreacted aglycon is much more hydrophobic than the corresponding glucuronide and thus will be well resolved on reversed phase systems. The cofactor, UDP glucuronic acid, and the byproduct, UDP, are both very hydrophilic and will be much less retained than the glucuronide of a hydrophobic compound. Finally, all the solvent systems described are based on $NH_4OAc$, a volatile buffer. Modifications to this system may be necessary in order to purify glucuronides of very hydrophilic compounds. Other reversed phase stationary supports, for example, phenyl silica, C-8 silica, and the like, can be used. The resolution of the two diastereomers is enhanced when the pH is lowered from 7.0 to 3.7, which would increase the fraction of the molecules in the zwitterionic form necessary for an intramolecular ionic interaction. In addition, increasing the ionic strength from 0.1% $NH_4OAc$ to 1% $NH_4OAc$ diminishes the resolution as would be expected if an intramolecular "salt bridge" were present.

Liver microsomes which can be used in the subject invention can be obtained from animal sources, for example, rabbit, bovine, and the like.

The temperature of incubation in the enzymatic step can be from about 20° to about 45° C.

The compounds of the invention, i.e., (+),(−)tropicamide O-β-D-glucuronide, (+)-tropicamide O-β-D-glucuronide, and (−)-tropicamide O-β-D-glucuronide are useful because of their absorption of ultraviolet light. These compounds can be incorporated in standard vehicles suitable for application to the human skin to produce compositions useful to prevent sunburn. For example, a one percent solution in corn oil applied to the skin absorbs ultraviolet light, and, thus, protects the skin. The invention compounds also can be used as ultraviolet absorbents in technical and industrial areas as follows:

(a) Textile materials; such textile materials may consist of natural materials of animal origin, such as wool or silk, or of vegetable origin, such as cellulosic materials of cotton, hemp, flax, or linen, and also semi-synthetic materials, such as regenerated cellulose, for example, artificial silk viscoses, including staple fibers of regenerated cellulose.

(b) Fibrous materials of other kinds (that is to say not textile materials) which may be of animal origin, such as feathers, hair, straw, wood, wood pulp or fibrous materials consisting of compacted fibers, such as paper, cardboard or compressed wood, and also materials made from the latter; and also paper masses, for example, hollander masses, used for making paper.

(c) Coating or dressing agent for textiles or paper.
(d) Lacquers or films of various compositions.
(e) Natural or synthetic resins.
(f) Hydrophobic oily, fatty or wax-like substances.
(g) Natural rubber-like materials.
(h) Cosmetic preparations.
(i) Filter layers for photographic purposes, especially for color photography.

Depending on the nature of the material to be treated, the requirements with regard to the degree of activity and durability, and other factors, the proportion of the light-screening agent to be incorporated in the material may vary within fairly wide limits, for example, from about 0.01 to 10%, and advantageously 0.1% to 2%, on the weight of the material which is to be directly protected against the action of ultraviolet rays.

The following examples are illustrative of the process and products of the invention, but are not to be construed as limiting. All percentages are by weight and all solvent mixture proportions are by volume unless otherwise noted.

EXAMPLE 1

Enzymatic preparation of (+,−)-tropicamide O-β-D-glucuronide

Four grams of a rabbit liver or bovine liver microsomal fraction (Sigma Chemical Co., St. Louis, Mo.) are suspended in 100 ml of a 75 mM tris hydrochloride buffer (pH=7.5-8.0). The microsomes are suspended by repeatedly drawing the mixture through a pipette tip. The microsomes are then pelleted by centrifugation at 100,000 g for 30 minutes. The supernatant is discarded, and the pellet is resuspended to 100 ml with a 150 mM tris hydrochloride (pH=7.5-8.0) solution, containing 200 mg (+,−)-tropicamide (Hoffman-LaRoche, Nutley, N.J., also disclosed in U.S. Pat. No. 2,726,245) and 1 gram of sodium uridine 5′-diphosphoglucuronic acid (Sigma Chemical Co.). After a 20 hr. incubation at 37° C., the reaction is terminated by heating to about 70° C., and centrifuging the reaction mixture. The desired product is in the supernatant. The yield of desired product is determined by high pressure liquid chromatography (HPLC) to be ~75%.

The HPLC conditions are as follows: a 0.47×25 cm C-18 μBondapak column (Waters Associates, Milford, Mass.) is eluted at 2 ml/min. with 0.1% NH4OAc (pH=5.75). After injection of the sample, a linear gradient to 60% methanol is applied to the column over a 20 minute period. The column eluant is monitored with an ultraviolet detector set at 254 nm. Under these conditions the reaction product elutes as a partially resolved doublet. On the basis of the chemical and spectral data presented below the two peaks are assigned as (+)-tropicamide O-β-D-glucuronide and (−)-tropicamide O-β-D-glucuronide.

EXAMPLE 2

Isolation of essentially pure (+),(−)tropicamide O-β-D-glucuronide.

The pH of the reaction mixture, obtained in Example 1, is adjusted to 5.75 with 1.26 ml of 10% NH4OAc (pH=5.75); 25 ml of methanol is added to the reaction, and the suspension is centrifuged at 44,000 g for 60 minutes. The supernatant is collected and loaded onto a 15 mm by 250 cm column of octadecyl derivatized silica (50-100μ particles) (Waters Associates) which had been equilibrated with an 80/20 solution of 0.1% NH4OAc (pH=5.75)/methanol. The column is washed at 3 ml/min. until the absorbance of the eluant at 254 nm is less than 0.05. Essentially pure (+),(−)-tropicamide O-β-D-glucuronide is then eluted with a 55/45 solution of 0.1% NH OAc (pH=5.75)/methanol. Unreacted (+,−)-tropicamide is eluted from the column with a 40/60 solution of 0.1% NH OAc (pH=5.75)/methanol. The desired product contains less than 1% of (+,−)-tropicamide contamination.

EXAMPLE 3

Separation of (+)- and (−)-tropicamide O-β-D-glucuronide

The two isomers are isolated from the mixture obtained in Example 2 as follows:

The two isomers are isolated by HPLC on a 0.39×30 cm column of C-18 μBondapak (Waters Associates). The column is equilibrated with 0.013 M NH4OAc (pH=3.7) containing 10% methanol at a flow rate of 2 ml/min. One minute after injection of the sample, the percentage of methanol in the eluant is raised to 22% in one minute. The two diastereomers elute at about eleven and thirteen minutes respectively. Retention times vary with column condition and the optimal concentration of methanol is normally determined with analytical injections. The two diastereomers are obtained in their essentially pure form.

Characterization of (+)- and (−)-tropicamide O-β-D-glucuronide.

The two reaction products (50 μg in 150 μl of 50 mM sodium phosphate, pH=6.8) are individually treated with ten Fishman units of E. coli β-glucuronidase (EC 3.2.1.31) at 37° C. for 1 hour. Both compounds are quantitatively hydrolyzed by the glucuronidase to products which were indistinguishable by HPLC from the starting material, (+,−)-tropicamide, in the 0.1% NH4OAc (pH=5.75)/methanol solvent system described above. The products are also indistinguishable from (+,−)-tropicamide when chromatographed on C-18 in a second solvent system consisting of 1% triethylammonium acetate (pH=7.0) eluted with a linear gradient to 50% acetonitrile in 25 minutes. These data show that both products contain an intact tropicamide moiety. The known specificity of this enzyme shows the presence of a glucuronic acid moiety and shows that the glycosidic linkage has the β configuration. The tropicamides released by glucuronidase treatment are individually converted back to the corresponding glucuronides using the conditions described above. These reactions produced single products, i.e., the tropicamide derived from glucuronidase treatment of component 1 yields only component 1, and the tropicamide derived from component 2 yields only component 2. Thus the two products are diastereomers which differ only in the configuration of the optically active carbon in the tropicamide moity.

The products of β-glucuronidase hydrolysis are further characterized by their rotation of 589 nm plane polarized light. These measurements show that the component which elutes earlier in the HPLC assay is dextrorotatory and the later eluting compound is levorotatory. Experiments with lesser amounts of E. coli glucuronidase show that the hydrolysis rate of (+)-tropicamide O-β-D-glucuronide is approximately twice as rapid as (−)-tropicamide O-β-D-glcuronide.

The ultraviolet spectra of (+),(−)-tropicamide, (+)-tropicamide O-β-D-glucuronide, and (−)-tropicamide O-β-D-glucuronide are recorded in a 0.05% NH₄OAc (pH=7.0) solution. All three samples have identical spectra with maxima at 257 nm (Emax=2140) and shoulders at 252 nm and 263 nm characteristic of a para substituted pyridone moiety.

The molecular weights of the two diastereomers are determined by direct chemical ionization (DCI) mass spectrometry and fast atom bombardment (FAB) mass spectrometry. The ammonia DCI spectrum of each isomer gives a quasi molecular ion at m/z=461 (M+H)+, confirming the molecular weight as 460. Similarly the zenon FAB spectrum of both isomers contains a series of ions at m/z=461 (M+H)+, m/z=483 (M+Na)+, and m/z=499 (M+K)+clearly showing a molecular weight of 460.

The infrared spectra in KBr pellets of the two tropicamide glucuronides both exhibit strong absorption bands centered at 3150 cm$^{-1}$ and 1400 cm$^{-1}$ confirming that the ammonium salt had been formed as expected. Both compounds also exhibit a broad band at 1600 cm$^{-1}$ which is consistent with the presence of both a carboxylate and a tertiary amide carbonyl. In addition, a shoulder at 3350 cm$^{-1}$ is consistent with the hydroxyl groups in the glucuronides.

The ammonium and other base salts of the compounds are useful in the same manner as the free acid form. If desired the ammonium salt can be converted to the free acid by means well known in the art, for example, by adjusting the pH of the ammonium salt solution with a weak acid so as not to cause hydrolysis of the diastereomer. Salts with both inorganic and organic bases can be formed with the free acid. For example, in addition to ammonium salt, there also can be formed the sodium, potassium, calcium, and the like, by neutralizing an aqueous solution of the free acid.

(+),(−)-Tropicamide O-β-D-glucuronic acid has the following formula:

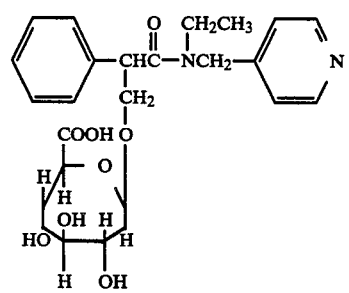

We claim:

1. A process for separating ammonium (+)-tropicamide O-β-d-glucuronic acid from ammonium (+),(−)-tropicamide O-β-D-glucuronic acid which comprises subjecting ammonium (+),(−)-tropicamide O-β-D-glucuronic acid to reversed phase liquid chromatography, and isolating ammonium (+)-tropicamide O-β-D-glucuronic acid free of ammonium (−)-tropicamide O-β-D-glucuronic acid.

2. A process for separating ammonium (−)-tropicamide O-β-D-glucuronic acid from ammonium (+),(−)-tropicamide O-β-D-glucuronic acid which comprises subjecting ammonium (+),(−)-tropicamide O-β-D-glucuronic acid to reversed phase liquid chromatography, and isolating ammonium (−)-tropicamide O-β-D-glucuronic acid free of ammonium (+)-tropicamide O-β-D-glucuronic acid.

* * * * *

UNITED STATES PATENT AND TRADEMARK OFFICE
CERTIFICATE OF CORRECTION

PATENT NO. : 4,629,792

DATED : Dec. 16, 1986

INVENTOR(S) : Walter C. Herlihy and Thomas H. Fraser

It is certified that error appears in the above-identified patent and that said Letters Patent is hereby corrected as shown below:

Col. 1, line 22: "urine using and" should read --urine and--.
Col. 2, line 18: "(+),(-)tropicamide" should read --(+),(-)-tropicamide--.
Col. 2, line 62: "(+),(-)tropicamide" should read --(+),(-)-tropicamide--.
Col. 4, line 8: "(+),(-)tropicamide" should read --(+),(-)-tropicamide--.
Col. 4, line 12: "NH4OAc" should read --$NH_4OAc$--.
Col. 4, line 23: "NH OAc" should read --$NH_4OAc$--.
Col. 4, line 25: "NH OAc" should read --$NH_4OAc$--.

UNITED STATES PATENT AND TRADEMARK OFFICE
CERTIFICATE OF CORRECTION

PATENT NO. : 4,629,792

DATED : Dec. 16, 1986

INVENTOR(S) : Walter C. Herlihy and Thomas H. Fraser

It is certified that error appears in the above-identified patent and that said Letters Patent is hereby corrected as shown below:

Col. 6, lines 15-26:

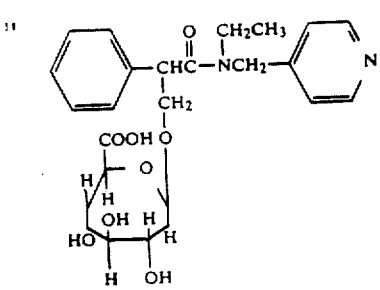 should read 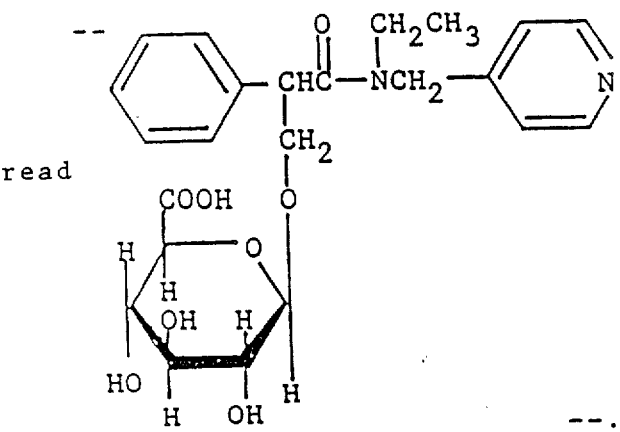

Signed and Sealed this

Twentieth Day of October, 1987

Attest:

DONALD J. QUIGG

Attesting Officer

Commissioner of Patents and Trademarks